United States Patent
Kilcher et al.

(10) Patent No.: US 7,648,361 B2
(45) Date of Patent: Jan. 19, 2010

(54) DENTAL DAM CLAMP

(75) Inventors: Beat Kilcher, Bosco Luganese (CH); Marco DaRold, Odogno (CH); Valerie Boscherini-DaSilva, Porza (CH); Luca Pedrinis, Osco (CH)

(73) Assignee: KerrHawe SA, Bioggio (CH)

(*) Notice: Subject to any disclaimer, the term of this patent is extended or adjusted under 35 U.S.C. 154(b) by 0 days.

(21) Appl. No.: 11/841,292

(22) Filed: Aug. 20, 2007

(65) Prior Publication Data

US 2008/0090205 A1  Apr. 17, 2008

Related U.S. Application Data

(60) Provisional application No. 60/829,590, filed on Oct. 16, 2006.

(51) Int. Cl.
*A61C 5/12* (2006.01)
(52) U.S. Cl. ..................................................... 433/139
(58) Field of Classification Search ......... 433/136–139, 433/155, 93–94
See application file for complete search history.

(56) References Cited

U.S. PATENT DOCUMENTS

| 658,179 | A | | 9/1900 | Ivory | |
|---|---|---|---|---|---|
| 4,007,530 | A | * | 2/1977 | Gaccione | 433/139 |
| 4,661,063 | A | * | 4/1987 | Levy | 433/139 |
| 4,773,857 | A | * | 9/1988 | Herrin | 433/138 |
| 2004/0197734 | A1 | * | 10/2004 | Mehdizadeh | 433/139 |
| 2005/0079356 | A1 | * | 4/2005 | Rathenow et al. | 428/408 |

FOREIGN PATENT DOCUMENTS

| DE | 196 32 084 C1 | | 2/1998 |
|---|---|---|---|
| DE | 19632084 | * | 2/1998 |
| GB | 586857 | | 4/1947 |
| WO | 94/22388 A1 | | 10/1994 |
| WO | WO 9422388 A1 | * | 10/1994 |

OTHER PUBLICATIONS

European Patent Office, European Search Report and Written Opinion in European Patent Application No. 07251003.5 dated Jan. 4, 2008.
European Patent Office, European Search Report and Written Opinion in European Patent Application No. 07251003.5 dated Mar. 14, 2008.

* cited by examiner

*Primary Examiner*—Cris L Rodriguez
*Assistant Examiner*—Matthew M Nelson
(74) *Attorney, Agent, or Firm*—Wood, Herron & Evans, LLP

(57) ABSTRACT

A dental dam clamp comprises first and second spaced, opposing jaws and respective first and second tooth engaging portions on the jaws. The first and second tooth engaging portions are positioned in confronting relation to one another and are biased toward one another by a resilient member when the jaws are moved outwardly from a free state defining a first position of the jaws. In one embodiment, first ends of the tooth engaging portions are spaced closer together than the second ends of the tooth engaging portions when the jaws are in the first position. The spacing between the first ends of the tooth engaging portions may be substantially the same as the spacing between the second ends of the tooth engaging portions when the jaws are moved outwardly to a second position. In another embodiment, the tooth engaging portions include friction-increasing surfaces to help secure the clamp to a tooth.

23 Claims, 2 Drawing Sheets

DENTAL DAM CLAMP

CROSS-REFERENCE

The present application claims the filing benefit of co-pending U.S. Provisional Patent Application No. 60/829,590, filed Oct. 16, 2006, which is incorporated by reference herein in its entirety.

TECHNICAL FIELD

The present invention relates generally to dental devices, and more particularly to a clamp for securing a dental dam to a patient's dental anatomy.

BACKGROUND

Dental dams are known in the art and have been used to isolate one or more teeth for treatment by a dental practitioner during root canal surgery or other procedures where it is desired to isolate and seal one or more teeth from the gingiva and dental cavity. Conventional dental dams typically comprise a thin sheet of rubber, or similar material, having one or more apertures for receiving one or more teeth therethrough while other teeth and the remaining dental anatomy are protected beneath the dam. After the apertures have been positioned over the desired teeth, the dam is generally stretched and secured to a frame. One or more dam clamps may be placed over the exposed teeth to prevent the dam from being pulled off the teeth as the dam is stretched and secured to the frame.

One drawback of prior dental dam clamps is the tendency for the clamps to slip off of the teeth while the dam is being stretched and secured to the frame, or worse, during a dental procedure. This tendency to slip off the teeth is often exasperated by non-uniform clamping between the teeth and the contact surfaces of the clamp.

When dental clamps are applied to molar teeth at the rear of the oral cavity, forceps or similar tools are generally used to position the clamps at the appropriate location. Another drawback of prior dental dam clamps is that the clamps often slip off or shift on the forceps, making precise placement difficult.

Yet another drawback of prior dental clamps, particularly metal clamps having sharp or pointed teeth for engaging the teeth, is the tendency to cause iatrogenic damage to the surfaces of the teeth. A need therefore exists for an improved dental dam clamp that overcomes these and other drawbacks of the prior art.

SUMMARY

The invention provides a dental clamp for securing a dental dam to the dental anatomy and which improves clamping uniformity, decreases the tendency to slip from the teeth and the forceps, and reduces or eliminates iatrogenic damage to the surfaces of the teeth. While the invention will be described in connection with certain embodiments, it will be understood that the invention is not limited to these embodiments. On the contrary, the invention includes all alternatives, modifications and equivalents as may be included within the scope of the invention.

In one embodiment, a dental dam clamp comprises first and second spaced, opposing jaws and respective first and second tooth engaging portions on the jaws. The first and second tooth engaging portions are positioned in confronting relation to one another and each has a first terminal end and a second terminal end. A resilient member coupled to the first and second jaws maintains the jaws in a first, free state, referred to as the first position, and biases the tooth engaging portions toward one another when the jaws are moved outwardly from the first position. In the first position, the first ends of the tooth engaging portions are spaced closer together than the second ends of the tooth engaging portions. When the jaws are moved outwardly to a second position, then the spacing between the first ends of the tooth engaging portions may be substantially the same as the spacing between the second ends of the tooth engaging portions.

In another embodiment, the clamp may include friction-increasing surfaces on each tooth engaging portion of the jaws. The friction-increasing surfaces may be physically formed on the tooth engaging portions, or may be a coating applied to the tooth engaging portions. In one embodiment, a friction-increasing coating may comprise particulate material applied to the tooth engaging portions.

In another embodiment, the clamp may include apertures on the respective jaws to facilitate installing the clamp on a tooth. The apertures are adapted to receive a portion of a tool suitable for moving the first and second jaws outwardly from the first position so that the jaws may be fitted over the tooth. The clamp may further include bearing surfaces adjacent the apertures and cooperating with the apertures to stabilize the clamp on the tool when the jaws are moved outwardly from the first position using the tool.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
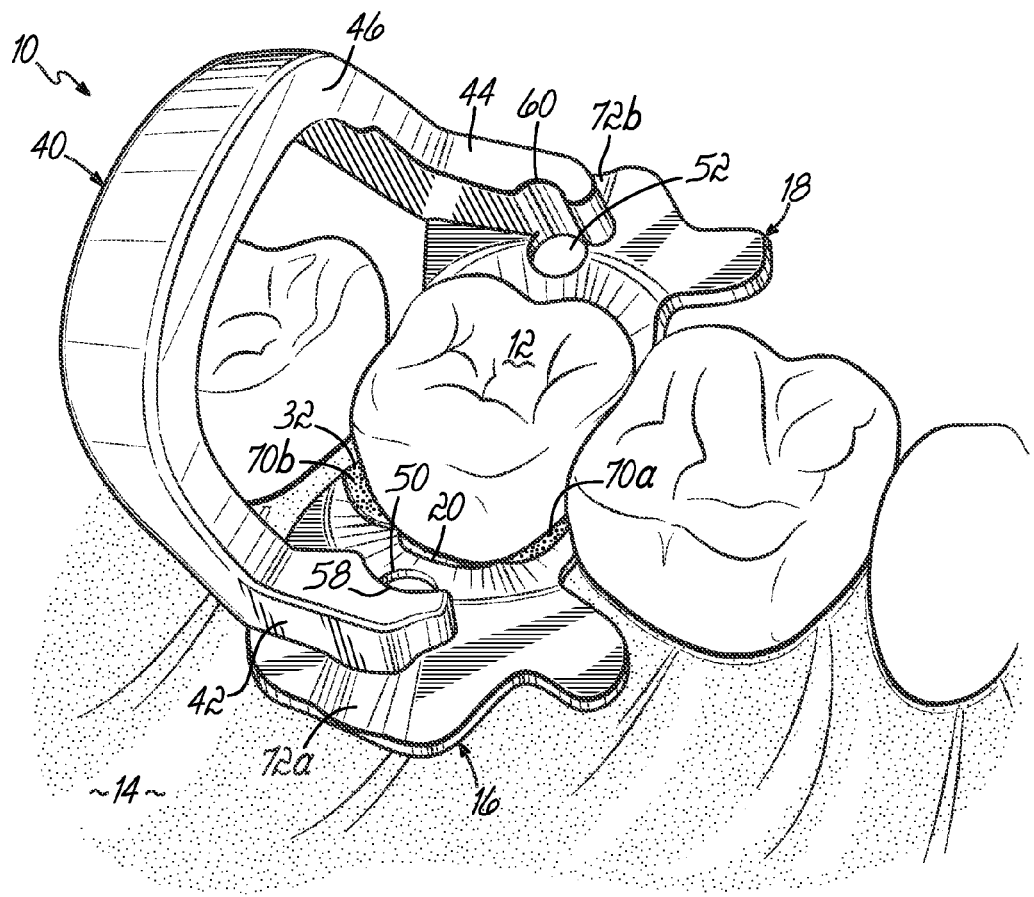
FIG. 1 is a perspective view of an exemplary dental dam clamp applied to the dental anatomy.

FIG. 1 depicts an exemplary dental dam clamp 10 applied to a tooth 12 and securing a dental dam 14 to a patient's dental anatomy. With continued reference to FIG. 1, and referring further to FIG. 2A, the dental dam clamp comprises spaced, opposing first and second jaws 16, 18 configured to engage the lingual, or palatal, and labial side surfaces of a tooth. The jaws 16, 18 have respective inner side edges 20, 22 generally facing one another and respective outer side edges 24, 26 facing away from one another. The inner side edges 20, 22 are generally arcuate in shape, to conform to the anatomy of a molar tooth 12. The inner side edges 20, 22 have respective first terminal ends 28, 30 and second terminal ends 32, 34. The inner side edges 20, 22 define tooth engaging portions of the clamp 10. These tooth engaging portions may comprise only the respective first terminal ends 28, 30 and second terminal ends 32, 34, or the tooth engaging portions may comprise the entire inner side edges 20, 22.

Figure 2A:
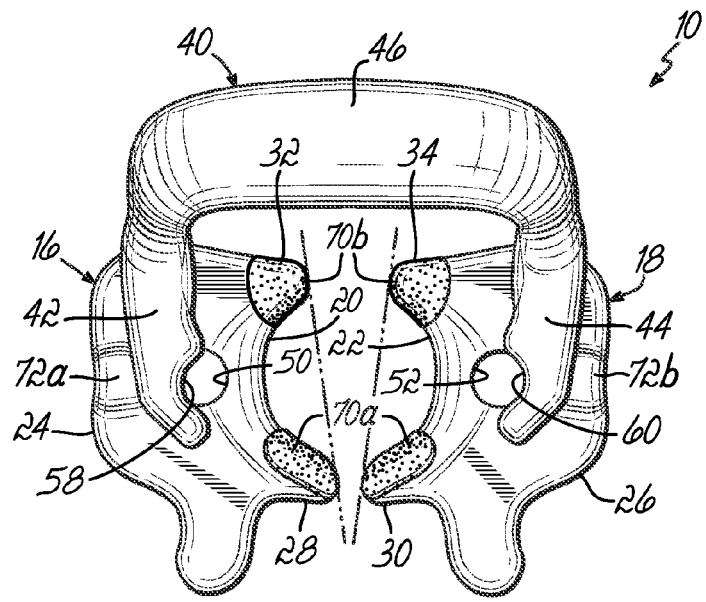
FIGS. 2A and 2B are top plan views of the dental dam clamp of FIG. 1.

The dental clamp 10 further includes a resilient member 40 extending between the first and second jaws 16, 18. In the embodiment shown, the resilient member 40 comprises first and second support arms 42, 44 associated with the first and second jaws 16, 18, respectively, and an arcuate bridge 46 extending between the first and second support arms 42, 44. In a free state of the clamp 10, the resilient member 40 maintains the first and second jaws 16, 18 in a first, spaced position relative to one another, as depicted in FIG. 2A. The resilient member 40 is configured to bias the tooth engaging portions on the first and second jaws 16, 18 toward one another when the first and second jaws 16, 18 are moved in directions outwardly from the first position.

In one embodiment, the first terminal ends 28, 30 of the inner side edges 20, 22 are spaced closer together than the second terminal ends 32, 34 of the inner side edges 20, 22 when the jaws 16, 18 are in the first position, as depicted in FIG. 2A. As the first and second jaws 16, 18 are caused to move outwardly relative to one another, for example when fitting the clamp 10 over a tooth 12, the resilient member 40 applies a biasing force to the first and second jaws 16, 18 which urges the inner side edges 20, 22 in directions toward one another. When the clamp 10 is fitted over a tooth 12, this biasing force clamps the tooth engaging portions securely against the side surfaces of the tooth 12. The in situ position of the clamp 10 secured against the tooth 12 may be referred to as the clamped state, or second position.

Figure 2B:
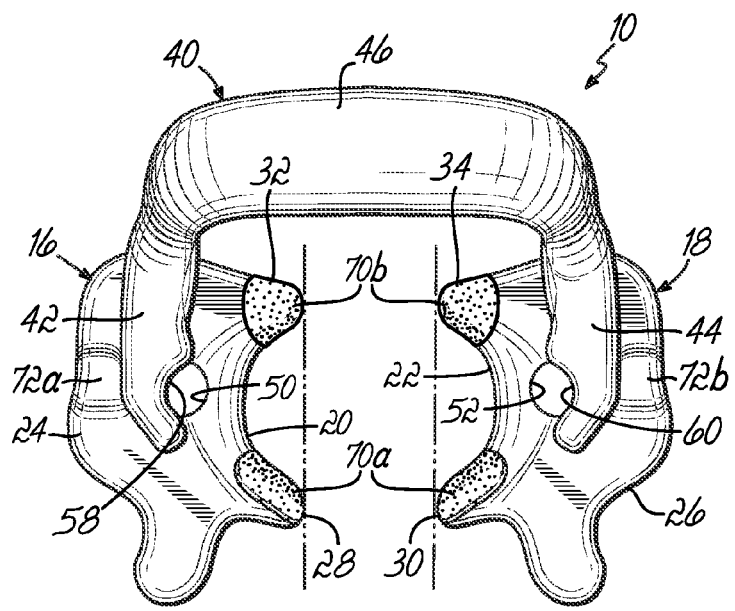

In another embodiment, clamp 10 is configured so that the distance between the first terminal ends 28, 30 of the inner side edges 20, 22 is substantially the same as the distance between the second terminal ends 32, 34 when jaws 16, 18 are moved outwardly to the second position, as depicted in FIG. 2B. This jaw configuration compensates for rotation and/or translation that may occur when the jaws 16, 18 are moved outwardly. Specifically, the first terminal ends 28, 30 may move outwardly more than the second terminal ends 32, 34 as the jaws 16, 18 are moved from the first position to the second position. The movement of both the first terminal ends 28, 30 and the second terminal ends 32, 34 is a combination of rotation and translation. If the distances along the jaws 16, 18 are equal in the first position and rotation and translation occurs during clamping, then the distances will be unequal in the second position, which may cause unequal clamping force along the tooth engaging portions of the clamp 10. Thus, a jaw configuration with unequal distances in the first position to compensate for rotation and translation of jaws 16, 18 upon movement to the second position may be desired to provide substantially uniform clamping force between the tooth 12 and the tooth engaging portions of the clamp 10. In one embodiment, first terminal ends 28, 30 are spaced closer together than the second terminal ends 32, 34 when jaws 16, 18 are in the first position, and first terminal ends 28, 30 and second terminal ends 32, 34 are equally spaced when jaws 16, 18 are in the second position. The distances in the first position and second position may be selected to accommodate different tooth sizes, as necessary.

Figure 4:
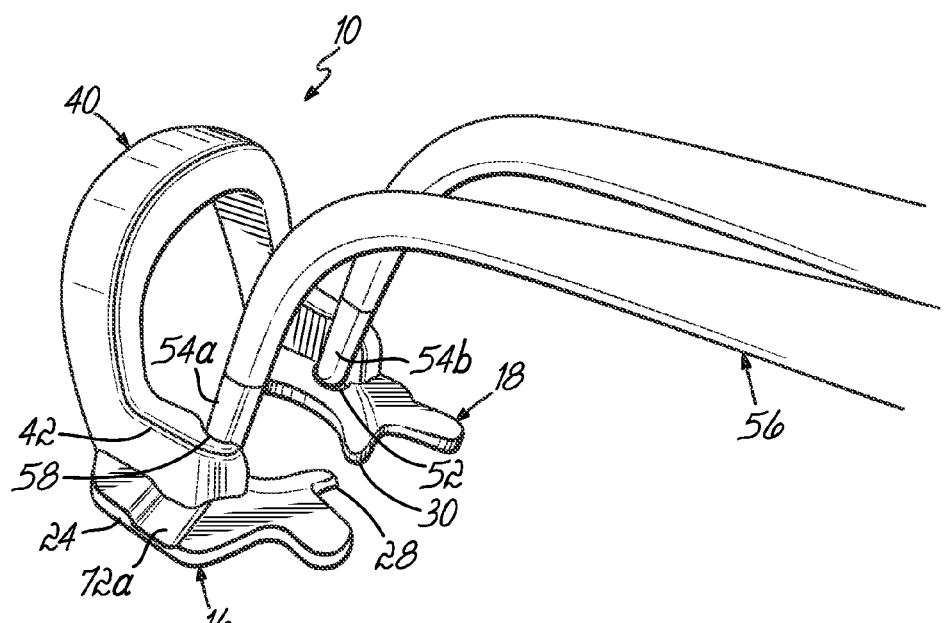
FIG. 4 is a perspective view illustrating a dental dam clamp supported on forceps for insertion onto a tooth.

With continued reference to FIGS. 1 and 2A, and further reference to FIG. 4, each jaw 16, 18 further includes an aperture 50, 52 therethrough, between the respective inner side edges 20, 22 and outer side edges 24, 26 for receiving the tips 54a, 54b of forceps 56 or similar tools which are suitable to grip the clamp 10 and facilitate spreading the first and second jaws 16, 18 apart so that the clamp 10 may be applied to a tooth 12. In the embodiment shown, the clamp 10 further includes bearing surfaces 58, 60 provided adjacent the apertures 50, 52 and configured to engage the tips 54a, 54b of the forceps 56 when the tips 54a, 54b are placed in apertures 50, 52 and manipulated to move the jaws 16, 18 outwardly from the first position. In the embodiment shown, the bearing surfaces 58, 60 comprise arcuate or V-shaped notches provided on portions of the support arms 42, 44 adjacent the apertures 50, 52. The bearing surfaces 58, 60 help to stabilize the clamp 10 when the clamp 10 is supported on forceps 56 for application to the tooth 12 of a patient. Moreover, the notched shape of the bearing surfaces 58, 60 permits more universal compatibility with available forceps having different tip configurations while maintaining good control of the clamp 10. Rotation of the clamp 10 is resisted because the tips of the forceps, regardless of their configuration, are located in the arcuate or V-shaped notches of the bearing surfaces 58, 60.

Figure 3:
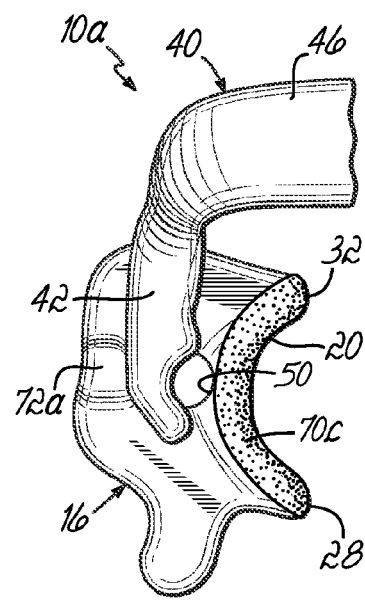
FIG. 3 is a partial plan view, similar to FIGS. 2A and 2B, illustrating another dental dam clamp.

In another embodiment, the first and second jaws 16, 18 may include one or more friction-increasing surfaces 70a, 70b, and/or 70c provided on the respective inner side edges 20, 22 to increase gripping of the jaws 16, 18 against a tooth 12. In one example, friction-increasing surface 70c may be provided along the entire length of the inner side edges 20, 22, as partially depicted in FIG. 3, which illustrates a portion of an alternative clamp 10a wherein similar features are similarly numbered. Alternatively, friction-increasing surfaces 70a and 70b may be applied to distinct portions of the inner side edges 20, 22, such as the first terminal ends 28, 30 and the second terminals ends 32, 34, respectively, as depicted in FIGS. 2A and 2B. The friction-increasing surfaces 70a, 70b, 70c may be physically formed on the jaws 16, 18, for example, as roughened or knurled surfaces, or as other physical features formed directly on the jaws 16, 18. Alternatively, the friction-increasing surfaces 70a, 70b, 70c may comprise a coating applied to desired areas of the jaws 16, 18.

In one embodiment, a friction-increasing coating comprises particulate material applied to the jaws 16, 18 at the first side edges 20, 22. The particles may be secured to the friction-increasing surfaces 70a, 70b, 70c, for example, using adhesives. Desirable adhesives should provide good adhesion to the material of the clamp 10, 10a and should be biocompatible. The adhesives should also be able to withstand chemicals that may be used during dental procedures, and should be able to be disinfected and/or sterilized so that the clamp 10, 10a may be reused. The polymerized adhesives should be sufficiently stiff, or hard, to hold the particles on the friction-increasing surfaces 70a, 70b, 70c of the clamp 10, 10a while permitting the particles to adapt themselves to the surfaces of the teeth, but should not be so stiff that the particles could damage the surfaces of the teeth. In one embodiment, the polymerized adhesive may have a hardness between about 30 Shore D to about 100 Shore D. Exemplary adhesives may include epoxy, acrylic-based, or silicone-based adhesives.

By way of example and not limitation, the particulate material may have an average grain size of approximately 10 microns to approximately 80 microns. The particles may have a cubic shape which is not too brittle, helps the particles better withstand pressures applied to the particles during use of the clamp 10, 10a, and reduces or eliminates damage to the surfaces of the teeth, compared to sharp-edged particles. It will be recognized, however, that other shapes may alternatively be used. The hardness of the particles may be selected to be higher than the hardness of the dentin and enamel of the teeth, but not so hard that it could damage the surfaces of the teeth. In one embodiment, the coating comprises particulate material having a Mohs hardness of approximately 8 to approximately 15. In yet another embodiment, the coating may comprise particulate material having a Mohs hardness of approximately 9 to approximately 12. In one embodiment, the coating comprises aluminum oxide ($Al_2O_3$) particles applied to the inner side edges 20, 22 of the respective jaws 16, 18. The aluminum oxide may be bonded to the inner side edges 20, 22, for example, using an epoxy resin suitable for adhering the aluminum oxide particulate material to the jaws 16, 18. In another embodiment, the coating may comprise particulate topaz, particulate corundum, particulate garnet, particulate fused zirconia, particulate silicon carbide, particulate boron carbide, particulate diamond, or any other particulate material suitable for increasing the friction of the jaws 16, 18 proximate the inner side edges 20, 22.

The exemplary dental clamp 10, 10a may be formed from any material suitable for clamping against tooth surfaces to retain a dental dam 14 on a tooth as described above. In one embodiment, the jaws 16, 18 and resilient member 40, or any portions thereof, may be formed from polymeric material such as polyetheretherketone (PEEK), polyphenylsulfone (PPSU), polyethylenimine (PEI), polyoxymethylene (POM), or any other polymeric material suitable for use as a dental clamp as described above. By way of example, PEEK exhibits good stability to chemical attack from chemicals used in dental procedures, and good stability under the stress conditions applied to the clamp 10, 10a. In one embodiment, the polymeric material is selected to resist chemical or heat sterilization such that the dental clamp 10, 10a may be reused.

In another embodiment, the dental clamp 10, 10a is formed at least partially from polymeric material and further comprises radiopaque filler dispersed in said polymeric material. For example, the radiopaque filler may comprise barium silicate, strontium silicate, yttrium trifluorides, or ytterbium trifluorides, or any other material suitable for use in dental applications and being opaque in x-ray photographs or under fluoroscopy. In the unfortunate event that a patient swallows the clamp, the radiopaque filler will facilitate its detection. The amount or radiopaque filler may be selected to ensure sufficient radiopacity so that the clamp 10, 10a can be detected, while also being sufficiently transparent that tooth structure covered by the clamp 10, 10a during use is visible in x-ray or fluoroscopic images. In contrast, tooth structure covered by conventional metal clamps is not visible in x-ray or fluoroscopic images.

The first and second jaws 16, 18 may further include a recess or flute 72a, 72b formed adjacent the outer side edges 24, 26. The flutes 72a, 72b facilitate slipping a dental dam 14 over the respective outer side edges 24, 26 of the clamp 10, 10a.

A dental dam clamp 10, 10a as described above may be used to secure a dental dam 14 to a person's dental anatomy, as depicted in FIG. 1. Once the dental dam 14 has been applied to the dental anatomy, with at least one tooth 12 projecting through the dam 14, a clamp 10, 10a may be positioned on forceps 56 adapted to facilitate moving the jaws 16, 18 and positioning the clamp 10, 10a relative to a desired tooth 12. The tips 54a, 54b of the forceps 56 may be inserted into the apertures 50, 52 on the respective jaws 16, 18, with the tips 54a, 54b also engaging the bearing surfaces 58, 60 for stability, as depicted in FIG. 4. The forceps 56 may be manipulated to move the jaws 16, 18 outwardly from the first position, or free state, of the clamp 10, 10a so that the clamp 10, 10a may be fitted over a tooth 12, such that the jaws 16, 18 are positioned on opposite sides of the tooth 12. Once the clamp 10, 10a is in the desired location, the forceps 56 may be manipulated to permit the jaws 16, 18 to be urged by the biasing force of the resilient member 40 so that the tooth engaging portions 70a, 70b, and/or 70c contact the tooth 12. In one embodiment, contact of the tooth engaging portions 70a, 70b, and/or 70c with the tooth 12 corresponds to the second position, or clamped state, described above, wherein the distance between the first terminal ends 28, 30 is substantially the same as the distance between the second terminal ends 32, 34.

While the present invention has been illustrated by the description of an embodiment thereof, and while the embodiment has been described in considerable detail, it is not intended to restrict or in any way limit the scope of the appended claims to such detail. Features disclosed herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A dental clamp for a single tooth, comprising:
   first and second spaced, opposing jaws;
   first and second tooth engaging portions on said first and second spaced, opposing jaws, respectively, said first and second tooth engaging portions positioned in confronting relation to one another, each of said first and second tooth engaging portions having a first terminal end and a second terminal end; and
   a resilient member operatively coupled to said first and second spaced, opposing jaws, said resilient member maintaining said first and second spaced, opposing jaws in a first, spaced position in a free state of the clamp, and biasing said first and second tooth engaging portions toward one another when said first and second spaced, opposing jaws are moved in a direction outwardly from said first, spaced position to a second, spaced position in a clamping state of the clamp;
   said first terminal ends of said first and second tooth engaging portions being spaced closer together than said second terminal ends of said first and second tooth engaging portions when said first and second spaced, opposing jaws are in said first, spaced position; and
   wherein a spacing between said first terminal ends of said first and second tooth engaging portions is substantially the same as a spacing between said second terminal ends of said first and second tooth engaging portions when said first and second spaced, opposing jaws are in said second, spaced position.

2. The dental clamp of claim 1, further comprising:
   a friction-increasing surface on each of said first and second tooth engaging portions of said clamp.

3. The dental clamp of claim 2, wherein said friction-increasing surface comprises a coating applied to said first and second tooth engaging portions.

4. The dental clamp of claim 3, wherein said coating comprises particulate material having an average grain size of approximately 10 microns to approximately 80 microns.

5. The dental clamp of claim 3, wherein said coating comprises particulate material having a Mohs hardness of approximately 8 to approximately 15.

6. The dental clamp of claim 3, wherein said coating comprises particulate material having a Mohs hardness of approximately 9 to approximately 12.

7. The dental clamp of claim 3, wherein said coating comprises particulate aluminum oxide.

8. The dental clamp of claim 7, wherein said particulate aluminum oxide is adhered to said tooth engaging portions with an epoxy resin.

9. The dental clamp of claim 3, wherein said coating comprises particulate silicon carbide.

10. The dental clamp of claim 3, wherein said coating comprises particulate diamond.

11. The dental clamp of claim 1, wherein at least one of said resilient member and said first and second spaced, opposing jaws are at least partially formed from polymeric material.

12. The dental clamp of claim 11, wherein said polymeric material is polyetheretherketone (PEEK), polyphenylsulfone (PPSU), polyethylenimine (PEI), or polyoxymethylene (POM).

13. The dental clamp of claim 11, further comprising a radiopaque filler dispersed in said polymeric material.

14. The dental clamp of claim 13, wherein said radiopaque filler is barium silicate, strontium silicate, yttrium trifluoride, or ytterbium trifluoride.

15. The dental clamp of claim 1, wherein said resilient member comprises:
    first and second support arms, each said first and second support arm associated with one of said first and second spaced, opposing jaws; and
    an arcuate bridge portion extending between said first and second support arms.

16. A dental clamp for a single tooth, comprising:
    first and second spaced, opposing jaws;
    first and second tooth engaging portions on said first and second spaced, opposing jaws, respectively, said first and second tooth engaging portions positioned in confronting relation to one another;
    a resilient member operatively coupled to said first and second spaced, opposing jaws, said resilient member maintaining said first and second spaced, opposing jaws in a first, spaced position in a free state of the clamp, and biasing said first and second tooth engaging portions toward one another when said first and second spaced, opposing jaws are moved in a direction outwardly from said first position;
    first and second apertures in said first and second spaced, opposing jaws, respectively, said first and second apertures adapted to receive a portion of a tool for moving said first and second spaced, opposing jaws outwardly from said first position for engagement with the tooth; and
    first and second bearing surfaces adjacent and distinct from said first and second apertures, respectively, said first and second bearing surfaces adapted to engage the tool and cooperating with said first and second apertures to stabilize the clamp on the tool when said first and second spaced, opposing jaws are moved outwardly from said first position using the tool.

17. The dental clamp of claim 16, further comprising:
    a friction-increasing surface on each of said first and second tooth engaging portions of said clamp.

18. The dental clamp of claim 16, wherein:
    said friction-increasing surface comprises a coating comprising particulate material on each of said first and second tooth engaging portions of said clamp; and
    a resin adhesive on each of said first and second spaced, opposing jaws and bonding said particulate material to said respective first and second tooth engaging portions.

19. A method of securing a clamp to a tooth, the clamp having first and second spaced, opposing jaws with respective tooth engaging portions, each tooth engaging portion having a first terminal end and a second terminal end, the method comprising:
    moving the first and second spaced, opposing jaws outwardly relative to one another from a free state wherein a distance between the respective first terminal ends of the tooth engaging portions is less than a distance between the respective second terminal ends of the tooth engaging portions; and
    positioning the first and second spaced, opposing jaws on opposite sides of a tooth.

20. The method of claim 19, further comprising:
    moving the first and second spaced, opposing jaws to engage the tooth with the tooth engaging portions, and wherein the distance between the respective first terminal ends of the tooth engaging portions is substantially equal to the distance between the respective second terminal ends of the tooth engaging portions.

21. The method of claim 19, further comprising:
    engaging the clamp with forceps adapted to facilitate moving the first and second spaced, opposing jaws and positioning the first and second spaced, opposing jaws relative to a tooth.

22. The method of claim 19, further comprising:
    positioning a dental dam over at least one tooth.

23. The dental clamp of claim 16, wherein said first and second bearing surfaces are aligned in registration with said first and second apertures, respectively.

* * * * *